United States Patent
Maloney et al.

(10) Patent No.: US 11,400,032 B2
(45) Date of Patent: Aug. 2, 2022

(54) TOOTH WHITENING ORAL CARE PRODUCT WITH CORE SHELL SILICA PARTICLES

(71) Applicant: COLGATE-PALMOLIVE COMPANY, New York, NY (US)

(72) Inventors: Venda Maloney, Piscataway, NJ (US); Suman Chopra, Monroe, NJ (US); Hallena Strotman, Somerset, NJ (US); Guisheng Pan, Philadelphia, PA (US)

(73) Assignee: Colgate-Palmolive Company, New York, NY (US)

(*) Notice: Subject to any disclaimer, the term of this patent is extended or adjusted under 35 U.S.C. 154(b) by 0 days.

(21) Appl. No.: 15/106,412

(22) PCT Filed: Dec. 19, 2014

(86) PCT No.: PCT/US2014/071511
§ 371 (c)(1),
(2) Date: Jun. 20, 2016

(87) PCT Pub. No.: WO2015/095709
PCT Pub. Date: Jun. 25, 2015

(65) Prior Publication Data
US 2016/0331653 A1    Nov. 17, 2016

Related U.S. Application Data

(63) Continuation of application No. PCT/US2014/071337, filed on Dec. 19, 2014, and a continuation of application No. PCT/US2014/071304, filed on Dec. 18, 2014, and a continuation of application No. PCT/US2014/071298, filed on Dec. 18, 2014.

(60) Provisional application No. 61/918,925, filed on Dec. 20, 2013, provisional application No. 61/918,938, filed on Dec. 20, 2013.

(51) Int. Cl.
| | |
|---|---|
| *A61K 8/25* | (2006.01) |
| *A61K 8/81* | (2006.01) |
| *A61K 8/34* | (2006.01) |
| *A61K 8/02* | (2006.01) |
| *A61Q 11/00* | (2006.01) |
| *A61K 8/46* | (2006.01) |
| *A61K 8/19* | (2006.01) |

(52) U.S. Cl.
CPC .............. *A61K 8/25* (2013.01); *A61K 8/0241* (2013.01); *A61K 8/0245* (2013.01); *A61K 8/19* (2013.01); *A61K 8/345* (2013.01); *A61K 8/466* (2013.01); *A61K 8/8164* (2013.01); *A61K 8/8176* (2013.01); *A61Q 11/00* (2013.01); *A61K 2800/43* (2013.01); *A61K 2800/621* (2013.01); *A61K 2800/651* (2013.01); *A61K 2800/92* (2013.01)

(58) Field of Classification Search
CPC ..................................................... A61K 9/4833
USPC ........................................................... 424/49
See application file for complete search history.

(56) References Cited

U.S. PATENT DOCUMENTS

| | | |
|---|---|---|
| 2,885,366 A | 5/1959 | Iler |
| 2,913,419 A | 11/1959 | Alexander |
| 3,537,815 A | 11/1970 | Burke, Jr. |
| 3,655,578 A | 4/1972 | Yates |
| 3,725,095 A | 4/1973 | Weidman, V et al. |
| 3,924,030 A | 12/1975 | Tatara et al. |
| 4,038,380 A | 7/1977 | Cordon |
| 4,336,245 A | 6/1982 | Wason |
| 4,340,583 A | 7/1982 | Wason |
| 4,568,540 A | 2/1986 | Akira et al. |
| 5,413,844 A | 5/1995 | Persello |
| 5,512,094 A | 4/1996 | Linton |
| 5,537,363 A | 7/1996 | Holcomb |
| 5,658,573 A | 8/1997 | Holcomb |
| 5,698,327 A | 12/1997 | Persello |
| 5,871,720 A | 2/1999 | Albanese et al. |
| 5,948,383 A | 9/1999 | Kuznicki et al. |
| 6,030,222 A | 2/2000 | Tarver |
| 6,221,326 B1 | 4/2001 | Amiche |
| 6,632,853 B2 | 10/2003 | Forschzent |
| 6,660,380 B1 | 12/2003 | Ishida et al. |
| 7,125,432 B2 | 10/2006 | Huang |
| 7,176,172 B2 | 2/2007 | Harding et al. |
| 7,267,814 B2 | 9/2007 | McGill et al. |
| 7,297,327 B2 | 11/2007 | Pilch et al. |
| 7,402,416 B2 | 7/2008 | Szeles et al. |

(Continued)

FOREIGN PATENT DOCUMENTS

| | | |
|---|---|---|
| CN | 86102002 | 9/1986 |
| CN | 86102002 | 10/1986 |

(Continued)

OTHER PUBLICATIONS

International Search Report and Written Opinion for priority application No. PCT/US2014/071511, dated Apr. 22, 2015.

(Continued)

*Primary Examiner* — Walter E Webb

(57) ABSTRACT

The present invention provides a tooth whitening oral care composition comprising: (i) a dye having a blue to blue-violet color with a hue angle in the CIELAB system ranging from 200 to 320 degrees; (ii) core shell silica particles, wherein each core shell silica particle comprises a silica core, and a surface of the silica core is etched with metal silicate; (iii) an orally acceptable carrier vehicle comprising a non-aqueous solvent; and wherein the composition comprises water in an amount of from 3 weight % to 30 weight %.

12 Claims, 2 Drawing Sheets

(56) References Cited

U.S. PATENT DOCUMENTS

| | | |
|---|---|---|
| 7,857,985 B2 | 12/2010 | Ishima et al. |
| 8,118,898 B2 | 2/2012 | Wakamiya et al. |
| 8,221,791 B1 | 7/2012 | Santra |
| 8,557,228 B2 | 10/2013 | Pan et al. |
| 8,609,068 B2 | 12/2013 | Hagar et al. |
| 8,834,857 B1 | 9/2014 | Winston et al. |
| 8,840,911 B2 | 9/2014 | Flugge-Berendes et al. |
| 9,028,605 B2 | 5/2015 | Hagar et al. |
| 9,138,600 B2 | 9/2015 | Batchelor et al. |
| 9,375,398 B2 | 6/2016 | Dreher |
| 9,744,112 B2 | 8/2017 | Szewczyk et al. |
| 10,064,794 B2 | 9/2018 | Xu et al. |
| 10,285,920 B2 | 5/2019 | Naser et al. |
| 10,300,028 B2 | 5/2019 | Tuffley |
| 10,369,091 B2 | 8/2019 | Pan et al. |
| 10,596,084 B2 | 3/2020 | Maloney et al. |
| 10,709,907 B2 | 7/2020 | Pan et al. |
| 2001/0031744 A1 | 10/2001 | Kosbab |
| 2002/0168324 A1 | 11/2002 | Amiche et al. |
| 2003/0206936 A1 | 11/2003 | Barclay et al. |
| 2005/0112161 A1 | 5/2005 | Luo et al. |
| 2006/0011337 A1 | 1/2006 | Paul |
| 2006/0027142 A1 | 2/2006 | Huang |
| 2006/0034780 A1 | 2/2006 | Guan et al. |
| 2006/0110307 A1 | 5/2006 | McGill et al. |
| 2006/0110338 A1 | 5/2006 | McGill et al. |
| 2006/0283095 A1 | 12/2006 | Mahulikar et al. |
| 2007/0003509 A1 | 1/2007 | Rawlings |
| 2007/0086960 A1 | 4/2007 | Tarver et al. |
| 2007/0186484 A1 | 8/2007 | Yamashita et al. |
| 2007/0275257 A1 | 11/2007 | Muraguchi et al. |
| 2008/0124295 A1 | 5/2008 | Duranton et al. |
| 2008/0152599 A1 | 6/2008 | Brignoli et al. |
| 2010/0189663 A1 | 7/2010 | Gallis et al. |
| 2011/0206746 A1 | 8/2011 | Hagar et al. |
| 2011/0206749 A1 | 8/2011 | Gallis et al. |
| 2012/0021034 A1 | 1/2012 | Zink et al. |
| 2012/0052025 A1 | 3/2012 | Porter et al. |
| 2012/0216719 A1 | 8/2012 | Hagar et al. |
| 2013/0129642 A1 | 5/2013 | Joiner et al. |
| 2013/0280409 A1 | 10/2013 | Mushock et al. |
| 2016/0296434 A1 | 10/2016 | Fei et al. |
| 2016/0331653 A1 | 11/2016 | Maloney et al. |
| 2016/0331663 A1 | 11/2016 | Maloney et al. |
| 2016/0338919 A1 | 11/2016 | Pan et al. |
| 2017/0266092 A1 | 9/2017 | Maloney et al. |
| 2020/0282240 A1 | 9/2020 | Pan et al. |

FOREIGN PATENT DOCUMENTS

| | | |
|---|---|---|
| CN | 1221393 | 6/1999 |
| CN | 1221393 A | 6/1999 |
| CN | 1625383 | 6/2005 |
| CN | 1625383 A | 6/2005 |
| CN | 1695447 | 11/2005 |
| CN | 1695447 A | 11/2005 |
| CN | 1739483 | 3/2006 |
| CN | 1739483 A | 3/2006 |
| CN | 1953658 A | 4/2007 |
| CN | 103274422 | 9/2013 |
| CN | 103342368 | 10/2013 |
| CN | 103429250 | 12/2013 |
| DE | 102013216381 | 2/2015 |
| EP | 345116 | 12/1989 |
| EP | 0345116 | 12/1989 |
| EP | 1935395 | 6/2008 |
| EP | 1935395 B1 | 6/2013 |
| GB | 804486 | 11/1958 |
| IL | 0000239533 | 8/2015 |
| JP | H11-511178 | 9/1999 |
| JP | H11-511178 A | 9/1999 |
| JP | 2002-047158 | 2/2002 |
| JP | 2002047158 | 2/2002 |
| JP | 2016-519077 | 6/2016 |
| KR | 20030061874 | 7/2003 |
| KR | 20110103934 | 9/2011 |
| KR | 20110103934 A | 9/2011 |
| KR | 20130074422 | 7/2013 |
| RU | 2214225 | 10/2003 |
| RU | 2275183 | 4/2006 |
| RU | 2417070 | 4/2011 |
| RU | 2485941 | 6/2013 |
| RU | 2496716 | 10/2013 |
| RU | 2527693 | 9/2014 |
| RU | 2582945 | 4/2016 |
| TW | 200745267 | 12/2017 |
| WO | 1994/006868 | 3/1994 |
| WO | 1997/046485 | 12/1997 |
| WO | 2002/049588 | 6/2002 |
| WO | 2002/096221 | 12/2002 |
| WO | 2005/107456 | 11/2005 |
| WO | 2008/070368 | 6/2008 |
| WO | 2009/001697 | 12/2008 |
| WO | 2009/112458 | 9/2009 |
| WO | WO 2012031785 | 3/2012 |
| WO | 2012/103037 | 8/2012 |
| WO | 2012/110995 | 8/2012 |
| WO | 2012110995 | 8/2012 |
| WO | 2013/072852 | 5/2013 |
| WO | 2013/089759 | 6/2013 |
| WO | WO 2013/089759 A1 | 6/2013 |
| WO | 2013/149323 | 10/2013 |
| WO | 2015/076817 | 5/2015 |
| WO | 2015/095709 | 6/2015 |
| WO | 2017/196299 | 11/2017 |

OTHER PUBLICATIONS

Corresponding International Search Report for PCT/US2014/071511.

Cardinal Search Report, Chemically Modified SiO2 Practical in Dental Products, Nov. 4, 2013.

Dr. Dipti Choksi and Dr. Barkha Idnani, A Research Review Article on Composite Material, Dept. of Conservative Dentistry and Endodontics, DDU, Sep. 30, 2013.

Cardinal Search Report, Chemically Modified SiO2 Practical in Dental Products, Supplemental Search, Nov. 5, 2013.

Rosario Ciriminna, et al., The Sol-Gel Route to Advanced Silica-Based Materials and Recent Applications, Jun. 19, 2013.

Alexei Smirnov, "Judge Paine hands down Holcomb Healthcare opinion." The Nashville Post, https://www.nashvillepost.com/business/health-care/nnedical-devices/article/20449550/judge-paine-hands-down-holcomb-healthcare-opinion downloaded Dec. 9, 2020, originally published Dec. 16, 2004, pp. 1-2. (Year: 2004).

Alexei Smirnov. "Legal dispute over Holcomb intellectual property expands." The Nashville Post, https://www.nashvillepost.com/home/article/20448692/legal-dispute-over-holcomb-intellectual-property-expands downloaded Dec. 9, 2020, published Apr. 1, 2004, pp. 1-3. (Year: 2004).

Angelo C. Pinto et al. "Separation of Acid Diterpenes of Copalfera cearensis Huber ex Ducke by Flash Chromatography Using Potassium Hydroxide Impregnated Silica Gel." Journal of the Brazilian Chemical Society, vol. 11, No. 4, 2000, pp. 355-360. (Year: 2000).

Anna Torrado, Manuel Valiente, Carlos A. Munoz, "Cleaning power and abrasivity of a new toothpaste based on ion-exchange resins." American Journal of Dentislly, vol. 17, No. 2, Apr. 2004, pp. 80-84. (Year: 2004).

BYU Cleanroom. KOH Etching. https://cleanroom.byu.edu/KOH accessed Sep. 27, 2018, 20 printed pages. (Year: 2018).

CaseText. "*Holcomb Health Care Services, LLC v. Quart Limited, LLC* (In re Holcomb Health Care Services, LLC)." https://casetext.com/case/in-re-holcomb-health-care-services downloaded on Dec. 9, 2020, originally published Dec. 14, 2004, pp. 1-79. (Year: 2004).

International Search Report for PCT/US2014/071298, dated May 28, 2015, pp. 1-8.

English translation of CN 1695447 A. Patent originally published in Chinese on Nov. 16, 2005. Translation obtained by examiner on Jun. 13, 2017. 6 printed pages.

(56) References Cited

OTHER PUBLICATIONS

Fertani-Gmati et al., 2011, "Thermochemistry and kinetics of silica dissolution in NaOH aqueous solution," Thermochimica Acta, 513:43-48.

Gahlaut et al., 2013, "Evaluation of antibacterial potential of plant extracts using Resazurin based microtiter dilution assay," International Journal of Pharmacy and Pharmaceutical Sciences 5(2):372-376.

Greenberg, 1957,"The depolymerization of silica in sodium hydroxide Solutions," Journal of Physical Chemistry, 61 (7):960-965.

International Search Report and Written Opinion of the International Searching Authority in International Application No. PCT/US2014/071304, dated May 28, 2015, pp. 1-10.

International Search Report and Written Opinion of the International Searching Authority in International Application No. PCT/US2014/071502, dated Apr. 22, 2015.

International Search Report and Written Opinion of the International Searching Authority in International Application No. PCT/US2017/067296, dated Mar. 23, 2018, pp. 1-11.

J Yamanaka, Y Hayashi, N Ise, T Yamaguchi. "Control of the surface charge density of colloidal silica by sodium hydroxide in salt-free and low-salt dispersions." Physical Review E, vol. 55 No. 3, Mar. 1997, pp. 3028-3036. (Year: 1997).

J. M. Rimsza, R. E. Jones, L. J. Criscenti, "Interaction of NaOH solutions with silica surfaces.", Journal of Colloid and nterface Science, vol. 516(2018), pp. 128-137. (Year:2018).

Lanlang Corporation, https://www.lanlangcorp.com/info/strong-base-anion-exchange-resin-example-41908792.html accessed Aug. 25, 2021, originally published Dec. 24, 2019, 5 printed pages. (Year: 2019).

Niibori et al., 2000, "Dissolution Rates of Amorphous Silica in Highly Alkaline Solution," Journal of Nuclear Science and Technology, 37(4):349-357.

Sten Ahrland, Ingmar Grenthe, and Bertil Noren. "The Ion Exchange Properties of Silica Gel, II. Separation of Plutonium and Fission Products from Irradiated Uranium." Acta Chemica Scandinavica, vol. 14, 1960, pp. 1077-1090. (Year: 1960).

Zhang et al., 2009, "Rattle-type silica colloidal particles prepared by a surface-protected etching process," Nano Research 2:583-591.

Zhuravlev, 2000, "The surface chemistry of amorphous silica. Zhuravlev model," Colloids and Surfaces: A: Physiochem. Eng. Aspects, 173:1-38.

Corresponding International Search Report for PCT/US2014/071298, dated May 28, 2015.

International Search Report and Written Opinion of the International Searching Authority in International Application No. PCT/US2014/071298, dated May 28, 2015.

International Search Report and Written Opinion of the International Searching Authority in International Application No. PCT/US2014/071304, dated May 28, 2015.

International Search Report and the Written Opinion of the International Searching Authority in International Application No. PCT/US2017/065673, dated Mar. 29, 2018.

Supelco, http://www.supelco.com.tw/B-11-Resins.pdf accessed Dec. 13, 2021, pp. 429-456. (Year: 2021).

TOOTH WHITENING ORAL CARE PRODUCT WITH CORE SHELL SILICA PARTICLES

CROSS-REFERENCE TO RELATED PATENT APPLICATIONS

The present application is a U.S. national stage application under 35 U.S.C. § 371 of PCT Application No. PCT/US2014/071511 filed Dec. 23, 2013, that claims priority to U.S. Provisional Patent Application Ser. No. 61/918,938 filed 20 Dec. 2013 and U.S. Provisional Patent Application Ser. No. 61/918,925, filed 20 Dec. 2013; and is a continuation of International Application No. PCT/US2014/071298 filed 18 Dec. 2014; International Application No. PCT/US2014/071304 filed 18 Dec. 2014; and International Application No. PCT/US2014/071337 filed 19 Dec. 2014, the entireties of which are incorporated herein by reference.

BACKGROUND

Many individuals are dissatisfied with their current tooth color. Thus, there is a desire for whiter teeth which can be achieved through the use of tooth whitening products. The whitening effect can be effected by chemically altering or removing the stain and/or changing the visual perception of the color of the teeth is known in the literature that the visual perception of a white substance can be altered through the deposition of an optical brightener, blue pigment or blue dye, especially one for which the hue angle (in the CIELAB scale) of the reflected or emitted light is between 200 to 320 degrees. This effect is commonly used in laundry detergent products to make white clothes appear "whiter" to the human eye. The same concept has been applied to tooth whitening as well. The natural off-white or yellow color of teeth can be made to appear whiter through the deposition of a blue substance onto teeth. Using pigments with a deposition aid, such as Gantrez® (copolymers of maleic anhydride and with methyl vinylether) in toothpaste to make teeth look whiter is disclosed in EP1935395B1.

It has been demonstrated in EP1935395 that the deposition of the blue substance from aqueous solutions onto teeth is optimal if the blue substance has limited solubility in saliva as is the case with a blue pigment. In addition, it was shown that the deposition is optimal if a high molecular weight polymer (MW>200,000 Da) such as Gantrez type polymers, PEGs, and cellulose ethers was present in the formulation to help the pigment adhere to the tooth. It is also known that other polymers, specifically low molecular weight hydroxypropylmethylcellulose polymers, can increase the deposition of blue pigment on teeth especially when the blue pigment is encapsulated within the matrix of a strip of the polymer.

Dyes have significantly different properties than pigments, in particular, dyes are much more soluble in water than pigments. This solubility of dyes makes them much more difficult to deposit and be retained on teeth. U.S. Pat. No. 6,030,222 discloses depositing dyes on teeth when blended with specific carriers. US Patent Application Publication 2012/0093905 discloses dyes coupled to certain polymers.

Blue dye, such as FD&C blue #1 or FD&C blue #5, is of a different chemical structure than blue pigment 15 so has a different solubility in water. In fact, the solubility of FD&C Blue #1 dye is >20 g/100 mL in water, as compared to <0.1 g/100 ml for blue pigment 15. The greater solubility of blue dye in water as compared to blue pigment will logically make it more difficult to deposit and retain blue dye on teeth in the hydrated environment of the oral cavity. To increase the deposition of blue dye Unilever has filed a patent application in which they covalently attach blue dye to a polymer backbone (US2012/0093905 A1). Luster White Now markets a toothpaste which claims to instantly whiten teeth in which a PVM/MA Copolymer is included in the formulation to presumably increase the retention of FD&C Blue #1 on teeth. Another granted patent (U.S. Pat. No. 6,030,222) claims to increase tooth-whitening through the absorption of blue dye into the pores of teeth, preferable from a hydrophilic carrier which aids absorption of the complementary dyes into the aqueous environment surrounding the teeth.

It would be desirable to have tooth whitening oral care products containing dyes that can produce superior temporary tooth whitening effects when incorporated into oral care products.

BRIEF SUMMARY

In one aspect, the present invention provides a tooth whitening oral care composition comprising:
(i) a dye having a blue to blue-violet color with a hue angle in the CIELAB system ranging from 200 to 320 degrees;
(ii) core shell silica particles, wherein each core shell silica particle comprises a silica core, and a surface of the silica core is etched with metal silicate;
(iii) an orally acceptable carrier vehicle comprising a non-aqueous solvent; and
wherein the composition comprises water in an amount of from 3 weight % to 30 weight %.

In a further aspect, the present invention provides a process for the preparation of a composition as defined in any preceding claim, the process comprising:
i) admixing an amount of silica particles in water with an amount of a base, the base comprising a metal ion, to produce the core shell silica particles, wherein each core shell silica particle comprises a silica core, and a surface of the silica core is etched with metal silicate;
ii) admixing the core shell silica particles formed in step i) with an orally acceptable carrier vehicle comprising a non-aqueous solvent, a dye having a blue to blue-violet color with a hue angle in the CIELAB system ranging from 200 to 320 degree, and an amount of water to produce a composition comprising from 3 weight % to 30 weight % water.

In another aspect, the present invention provides a method for whitening teeth comprising administering a composition according to the present invention to the oral cavity of a subject in need thereof.

Further areas of applicability of the present invention will become apparent from the detailed description provided hereinafter. It should be understood that the detailed description and specific examples, while indicating the preferred embodiment of the invention, are intended for purposes of illustration only and are not intended to limit the scope of the invention.

DETAILED DESCRIPTION

Figure 1:
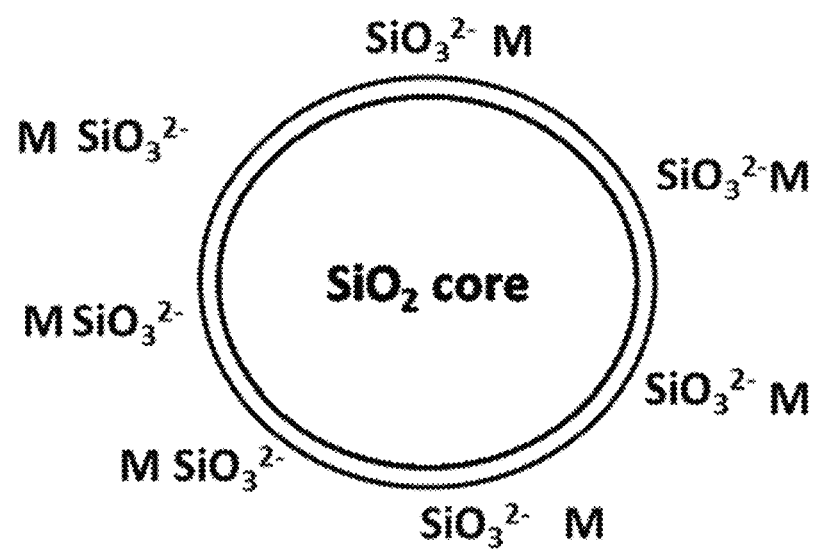
FIG. 1 depicts the structure of an exemplary core shell silica particle according to some embodiments of the present invention.

The following description of the preferred embodiment(s) is merely exemplary in nature and is in no way intended to limit the invention, its application, or uses.

The present invention provides a tooth whitening oral care composition comprising:
(i) a dye having a blue to blue-violet color with a hue angle in the CIELAB system ranging from 200 to 320 degrees;
(ii) core shell silica particles, wherein each core shell silica particle comprises a silica core, and a surface of the silica core is etched with metal silicate;
(iii) an orally acceptable carrier vehicle comprising a non-aqueous solvent; and
wherein the composition comprises water in an amount of from 3 weight % to 30 weight %.

We have surprisingly found that when the surface chemistry of silica is modified with a strong base the resulting particle can increase the retention of blue dye on the surface, providing a novel whitening agent. This novel material consisting of a silica core etched with silicate is referred to as core shell silica (CSS). It is understood that in some embodiments the blue dye forms a non-covalent complex with the CSS particles, in particular when the dye comprises a metal ion.

Dye

The dye should have a hue angle, h, in the CIELAB system of from 200 to 320 degrees, more particularly between 250 and 290 degrees. The dye may be a blue dye such as FD&C Blue#1, FD&C Blue #2, D&C Blue #4, CI Food Blue 5, Acid Blue 1, or a mixture thereof. The dye may comprises a mixture of one or more blue dyes and one or more red dyes.

A detailed description of hue angle may be found on p. 57 of Color Chemistry (Synthesis, Properties, and Applications of Organic Dyes and Pigments), 3rd edition by H. Zollinger published by Wiley-VCH (2001). While the preferred single dyes are blue or violet, the same effect may be achieved through mixing dyes outside of this h range; for example, such a hue angle may also be obtained by mixing a red and blue dye to yield a blue or blue-violet shaded dye. Typically, the dye is capable of reflecting sufficient light such that the treated tooth is perceivably whiter than its initial color. Preferably, the dye is colored such that its natural color is within the violet-red to green-blue color, typically from violet to blue.

Preferred dyes are water soluble dyes. The term "water-soluble" in this particular context generally means that the dye has an aqueous solubility of at least 10 g/L at 25° C., most preferably at least 100 g/L at 25° C. (where the solubility is determined in un-buffered distilled water). Triarylmethane dyes are examples of water soluble dyes useful in the present invention. In some embodiments, dyes useful herein are anionic triphenylmethane dyes, and especially diaminotriphenylmethane dyes containing from two to four sulphonate groups, such as those corresponding to general formula (I):

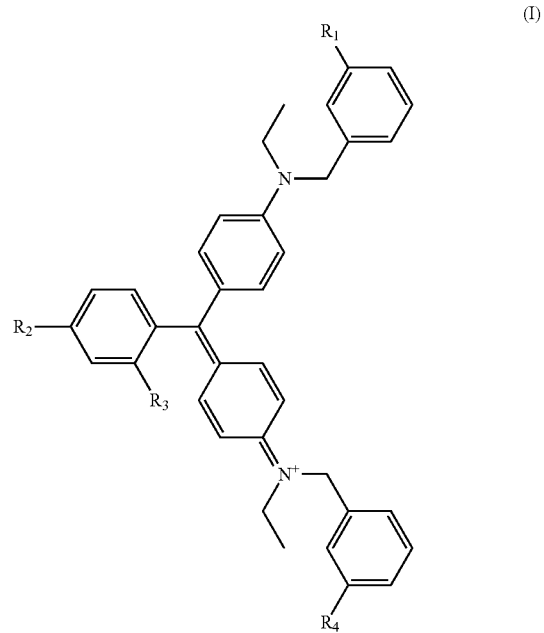

in which $R_1$, $R_2$, $R_3$ and $R_4$ are monovalent moieties which are each independently selected from hydrogen (—H), hydroxyl (—OH), halo (e.g. —Cl) and sulphonate (—$SO_3^-$) groups, with the proviso that at least two of $R_1$ to $R_1$ are sulphonate groups.

An example of a dye useful herein is FD&C Blue #1, also known as Brilliant Blue FCF (Blue 1) as well as other commercial names, which corresponds to general formula (I), wherein $R_2$ is —H and $R_1$, $R_3$, and $R_4$ are sulphonate groups. FD&C Blue #1 (CAS No. [3844-45-9]) is a colorant for foods and other substances to induce a color change. It is denoted by E number E133 and has a color index of 42090 (CI 42090). It has the appearance of a reddish-blue powder. It is soluble in water, and the solution has a maximum absorption at about 628 nanometer. It is a synthetic dye produced using aromatic hydrocarbons from petroleum. It is usually a disodium salt. The diammonium salt (D&C Blue #4) has CAS No. [2650-18-2]. Calcium and potassium salts are also known. Other dyes useful herein are FD&C Blue #2 (Indigo Carmine, CI 73015, CAS No. [860-22-0]), CI Food Blue 5 (CI 42051; also known as Acid Blue 3, CAS No. [3536-49-0]), Acid Blue 1 (CI 42045, CAS No. [129-17-9]) and the like. In some embodiments, the dye is FD&C Blue#1, FD&C Blue #2, D&C Blue #4, CI Food Blue 5, Acid Blue 1, or a mixture thereof.

Mixtures of dyes also can be used even if an individual dye has a hue angle outside the desired range as long as the mixture of dyes will be within the range. For example, red dyes, e.g., FD&C Red #3, FD&C Red #40, and the like, can be used. In one embodiment FD&C Blue #1 is used in combination with FD&C Red#40.

Delta b* is a magnitude of color change along a yellow-blue axis, negative delta b* corresponding to reduced yellowness.

The amount of dye in the oral care composition can be from 0.001 to 2 weight %, from 0.002 to 1.5 weight %, from 0.003 to 1.25 weight %, from 0.004 to 1 weight %, from 0.005 to 0.5 weight %, from 0.0075 to 0.25 weight %, from 0.01 to 0.1 weight %, from 0.02 to 0.07 weight %, or from 0.03 to 0.05 weight %. In some embodiments, the amount of dye in the oral care composition is about 0.03 weight %. In some embodiments, the amount of dye in the oral care composition is about 0.05 weight %. The dye may be uniformly spread throughout the composition or, it may be dispersed in a second phase such as a stripe or other coextruded second phase. Such "dual phase" compositions have the advantage that the phases may be differently colored, presenting a more visually attractive product to the consumer.

In some embodiments a blue pigment may be used instead of a dye.

In some embodiments, the composition is free from peroxide whitening agents. By "free from peroxide whitening agents", it is meant that the composition contains less than 0.1 weight %, less than 0.05 weight %, or less than 0.01 weight % peroxide whitening agents; or substantially no peroxide whitening agents; or that the composition contains no peroxide whitening agents. The tooth whitening effect of the oral care compositions of the present invention is provided by the presence of the dye, rather than by the presence of any peroxide whitening agents.

Description of the Core Shell Silica Particles

Core shell silica particles are prepared by etching silica ($SiO_2$) with a base to form core(Silica)-shell(metal silicate) structured colloids. For example using NaOH as the base, core($SiO_2$)-shell($Na_2SiO_3$) structured colloids are formed. The reaction is as follows:

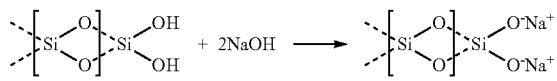

The $Na_2SiO_3$ molecules contribute 2 negative charges with 2 Na+ counter ions on the colloidal core-shell silica particle surface.

A surface of the silica core is etched with metal silicate. The term "etched" means that a surface of the silica core is dissolved, and metal silicate is formed on top of the silica core. The process for making the core shell silica particles comprises etching the original silica in order to form the metal silicate, such as $Na_2SiO_3$. The reaction of the silica particle with base causes a reduction in the diameter of the silica particle to form a silica core, and metal silicate is formed on top of the silica core. The $Na_2SiO_3$ layers are not additional layers coated on top of the original surface of the silica.

Typically the metal silicate is:
i. a metal silicate of a monovalent metal ion; or
ii. a metal silicate of; a monovalent metal ion and one or more of a of a divalent metal ion, a trivalent metal ion, and a tetravalent metal ion.

The metal silicate optionally comprises the formula $M^1_2SiO_3 \cdot x\, H_2O$, wherein M is a group I metal, and x is from 0 to 10. The metal silicate may be anhydrous, i.e. x=0, or may be hydrated. Preferably, M is Na or K.

The surface of the silica core may be the outer surface of the silica core (see FIG. 1).

Figure 2:
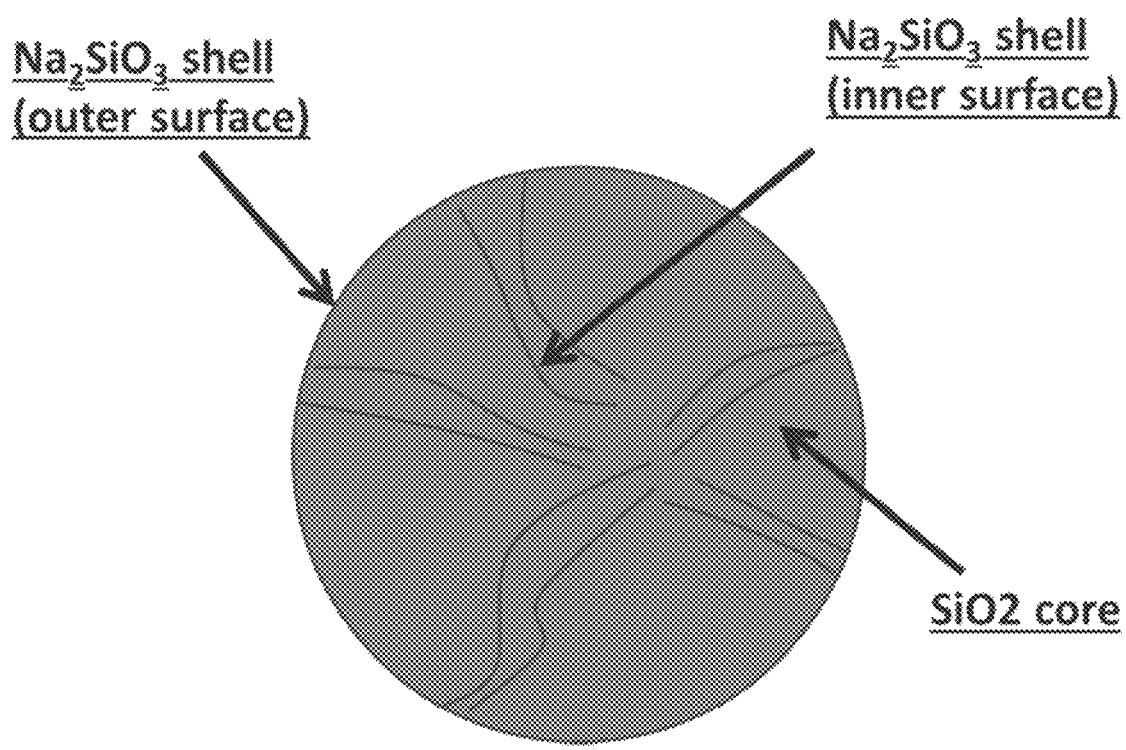
FIG. 2 depicts the strucutre of an exemplary core shell silica particle according to further embodiments of the present invention.

Alternatively, or in addition, the surface of the silica core may be an internal surface of the silica core (see FIG. 2).

In one embodiment the outer 10 nm depth of each particle comprises from 0.1 to 10, optionally 0.1 to 2 weight % $M^1_2SiO3 \cdot xH_2O$.

In one embodiment the outer 10 nm depth of each particle has the general formula:

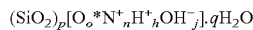

wherein O* is oxygen in the silicate form; M is a group I metal ion; p, o, n, h, j and q are the atomic percentages of each component (p is the atomic percentage of $SiO_2$, O is the atomic percentage of oxygen in the silicate form, m is the atomic percentage of group I metal, h is the atomic percentage of H+, j is the atomic percentage of OH−, and q is the atomic percentage of $H_2O$); and the total charge of each core shell silica particle is zero.

Typically the atomic percentage for each component except H+ is determined by electron spectroscopy for chemical analysis (ESCA).

Optionally, the outer 10 nm depth of each particle has one of the following compositions:

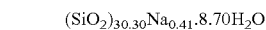

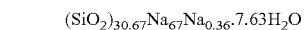

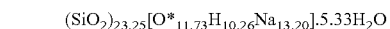

In one embodiment the metal silicate is a silicate of a monovalent metal ion and one or more of a divalent metal ion, a trivalent metal ion, and a tetravalent metal ion. These types of CSS particles are typically formed when the monovalent ions are displaced by divalent and/or trivalent and/or tetravalent ions.

Typically, the metal silicate comprises a silicate of a group 2 metal ion, a transition metal ion, a group 13 metal ion, a group 14 metal ion or mixtures thereof. Optionally, the metal silicate comprises a silicate of $Ca^{2+}$, $Mg^{2+}$, $Zn^{2+}$, $Sn^{2+}$, $Sr^{2+}$, $Al^{3+}$, $Zr^{4+}$, $Ti^{4+}$, $Fe^{3+}$, $Fe^{2+}$, $Mo^{2+}$, $Co^{2+}$, $Ni^{2+}$, $Mn^{2+}$, $Cu^{2+}$, $Pd^{2+}$, $Mo^{2+}$, $Ru^{2+}$ or mixtures thereof.

Optionally the metal silicate comprises the formula $M^2SiO_3 \cdot x\, H_2O$, wherein $M^2$ is a divalent metal ion, and x is from 0 to 10. $M^2$ may be selected from the group consisting of Zn, Ca, Mg, Sn, and Sr, optionally wherein $M^2$ is Zn.

In another embodiment, each core shell silica particle comprises a silica core, and a surface of the silica core etched with metal silicate, the core shell silica particles prepared by:
i) admixing an amount of silica particles in water with an amount of a base, wherein the base comprises a monovalent metal ion, to produce core shell silica particles, each core shell silica particle comprising a silica core, and a surface of the silica core etched with a silicate of the monovalent metal ion; and
ii) reacting the core shell silica particles formed in step i) with a metal salt comprising a second metal ion, to form core shell silica particles comprising silicate of the second metal ion on the surface of the silica core.

It will be understood that the second metal ion typically displaces the monovalent metal ion from the metal silicate on the surface of the silica core. There may be from 5-95 weight % of the monovalent metal ion displaced by the second metal ion, optionally 25 to 65 weight %. The amount of monovalent metal ion displaced by the second metal ion may be 1, 2, 5, 10, 15, 20, 30, 40, 50, 60, 70, or 80 weight %.

In a preferred embodiment the monovalent metal ion is a group 1 metal ion. Particularly preferred as the monovalent metal ion is a sodium ion or potassium ion.

The base is not especially limited, provided it comprises the monovalent metal ion. The base is typically a strong base. The base may be selected from the group consisting of sodium hydroxide, potassium hydroxide, sodium carbonate, potassium carbonate, trisodium phosphate, disodium phosphate, potassium phosphate, dipotassium phosphate, tetrasodium pyrophosphate, and tetrapotassium pyrophosphate.

Sodium or potassium hydroxide are preferred bases. The base may have a pKb value in the range 0.1 to 3. For example sodium hydroxide has a pKb of 0.2, and potassium hydroxide has a pKb of 0.5.

The second metal ion is not especially limited provided it can displace the monovalent metal ion from the silicate of the monovalent metal ion. The second metal ion may be a divalent metal ion, a trivalent metal ion, a tetravalent metal ion or mixtures thereof. Most preferably the second metal ion is a divalent metal ion. The second metal ion may be a group 2 metal ion, a transition metal ion, a group 13 metal ion, a group 14 metal ion or mixtures thereof. Preferably the second metal ion is $Ca^{2+}$, $Mg^{2+}$, $Zn^{2+}$, $Sn^{2+}$, $Sr^{2+}$, $Al^{3+}$, $Zr^{4+}$, $Ti^{4+}$, $Fe^{3+}$, $Fe^{2+}$, $Mo^{2+}$, $Co^{2+}$, $Ni^{2+}$, $Mn^{2+}$, $Cu^{2+}$, $Pd^{2+}$, $Mo^{2+}$, $Ru^{2+}$ or mixtures thereof. In a particularly preferred embodiment the second metal ion is $Zn^{2+}$.

By changing the first and second metal ions, core shell silica particles with different utilities can be provided. For example Zn—CSS are useful as antibacterial agents and anti-malodor agents, with a taste profile which is better than the taste profile of zinc salts such as $ZnCl_2$. The CSS particles retain their antibacterial and/or antimalor properties when in the dye composition. For example, blue toothpaste was prepared using blue #1 dye and it reduced malodor/or kill bacteria in saliva with the same efficacy as Total toothpaste.

The silicates may be hydrated or anhydrous.

It will be understood that the ability of ions of the metal silicate on an internal or outer surface of the CSS particles to be displaced is also behind the utility of the CSS particles as anti-tartar agents. Free calcium ions in saliva displace the monovalent metal ions and/or the second metal ions of the CSS particles, leading to a reduction in the concentration of calcium ions in saliva. This leads to a reduction in the formation of $Ca_3(PO_4)_2$, the main constituent of tartar. CSS particles with a higher weight % of metal silicate are better tartar control agents because they contain more sites available for calcium ion chelation.

In one embodiment the silicate of the monovalent metal ion formed in step i) comprises the formula $M^1_2{:}SiO_3.x\,H_2O$, wherein $M^1$ is a monovalent metal ion, optionally a group I metal ion, and x is from 0 to 10. $M^1$ is preferably $Na^+$ or $K^+$.

The silicate of the second metal ion formed in step ii) typically comprises the formula $M^2SiO_3.x\,H_2O$, wherein $M^2$ is a divalent metal ion, and x is from 0 to 10. $M^2$ is preferably selected from the group consisting of $Zn^{2+}$, $Ca^{2+}$, $Mg^{2+}$, $Sn^{2+}$, and $Sr^{2+}$.

The metal salt may be selected from the group consisting of a metal acetate, metal borate, metal butyrate, metal carbonate, metal halide, metal citrate, metal formate, metal gluconate, metal glycerate, metal glycolate, metal lactate, metal oxide, metal phosphate, metal picolinate, metal proprionate, metal salicylate, metal silicate, metal stearate, metal tartrate, metal undecylenate and mixtures thereof. In a preferred embodiment the metal salt is a metal halide. Most preferably, the metal halide is a metal chloride. Examples are $ZnCl_2$, $SnCl_2$, $SrCl_2$, $AlCl_3$, $FeCl_3$, $TiCl_4$, and $ZrCl_4$. In a particularly preferred embodiment the metal salt is a zinc salt. The metal salt may be a zinc salt selected from the group consisting of zinc acetate, zinc borate, zinc butyrate, zinc carbonate, zinc chloride, zinc citrate, zinc formate, zinc gluconate, zinc glycerate, zinc glycolate, zinc lactate, zinc oxide, zinc phosphate, zinc picolinate, zinc proprionate, zinc salicylate, zinc silicate, zinc stearate, zinc tartrate, zinc undecylenate and mixtures thereof. The most preferred zinc salt is zinc chloride.

In a preferred embodiment the silicate of the second metal ion comprises $ZnSiO_3.xH_2O$, wherein x is from 0 to 10.

In one embodiment the surface of the silica core is the outer surface of the silica core. In addition or as an alternative the surface of the silica core may be an internal surface of the silica core.

The silicate of the second metal ion may comprise at least 5 weight %, 10 weight %, 20 weight %, 30 weight %, 40 weight %, 50 weight %, 60 weight %, or 95 weight % of the total metal silicate of the CSS particles.

The outer 10 nm depth of each particle may comprise from 0.1 to 10 weight % metal silicate. In one embodiment the outer 10 nm depth of each particle has the general formula:

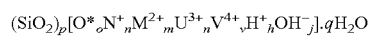

wherein O* is oxygen in the silicate form; N is a monovalent metal ion; M is a divalent metal ion; U is a trivalent metal ion; V is a tetravalent metal ion; p, o, n, m, u, v, h, j and q are the atomic percentages of each component; and the total charge of each core shell silica panicle is zero.

The atomic percentage for each component except H+ is typically determined by electron spectroscopy for chemical analysis (ESCA). In one example, using ESCA data, the following elements were detected:

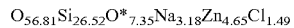

By setting the total electric charge to zero by adding H+ and water, we conclude that in one embodiment the outer 10 nm depth of each particle may have the following composition:

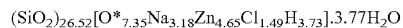

In one embodiment, the core shell silica particles comprise up to 20 weight % total metal.

In one embodiment, the d(0.5) value of the particles is from 5 nm to 50 µm.

The d(0.5) value of the particles may be from 26 µm to 40 µm. Particles having a d(0.5) value within this range are typically translucent. Translucent particles are those which allow light to pass through, although it is not possible to see an image through the particles. This is distinguished from transparent compositions which allow light to pass through and an image can be seen through the composition. Methods for determine particle size are well known in the art. For example particle size may be determined using light scattering methodologies, such as using the Mastersizer 2000, Hydro 2000S, Malvern Instruments Limited.

The d(0.5) value of the particles may be from 18 µm to 25 µm. The d(0.5) value of the particles may be from 10 µm to 15 µm. The d(0.5) value of the particles may be from 5 nm to 12 nm.

The d(0.5) or d50 of the particles is the diameter (typically in microns) that splits the distribution with half the population above and half below this diameter. It will be noted that this parameter is a value for a population of particles, and that the diameter of an individual particle may be larger or smaller than the d(0.5) values described herein. The Dv50 (or Dv0.5) is the median for a volume distribution, Dn50 is used for number distributions, and Ds50 is used for surface distributions. In the present context, d(0.5) will be used to refer to the median particle size for a volume distribution.

The d(0.1) value of the particles is the diameter that splits the distribution with 10% of the population below and 90% above this diameter.

The d(0.9) value of the particles is the diameter that splits the distribution with 90% of the population below and 10% above this diameter.

A value used to describe the distribution width of the particle size distribution is the span:

$$\text{Span} = (d(0.9) - d(0.1))/d(0.5)$$

The span of the core shell silica particles according to the present invention is typically from 1.5 to 3.

In a preferred embodiment, the CSS have a d(0.1) of from 10 to 13 μm, a d(0.5) of from 30 to 33 μm, and a d(0.9) of from 61 to 64 μm.

In another preferred embodiment, the CSS have a d(0.1) of from 6 to 9 μm, a d(0.5) of from 18 to 21 μm, and a d(0.9) of from 41 to 45 μm.

In a further preferred embodiment, the CSS have a d(0.1) of from 3 to 5 μm, a d(0.5) of from 11 to 14 μm, and a d(0.9) of from 33 to 36 μm.

In preferred embodiments, the d(0.5) value of the CSS particles is less than the mean diameter of a human dentin tubule. This allows the CSS particles to enter the dentin tubules, which may be exposed on damage to the protective enamel layer. In human teeth, dentin tubules taper from the inner to the outermost surface, and have a mean diameter of 2.5 μm near the pulp, 1.2 μm in the middle of the dentin, and 0.9 μm at the dentino-enamel junction (see http://www.slideshare.net/DrAbusaliamah/history-of-dentin). Thus the d(0.5) value of the CSS particles is preferably less than 0.9 μm. In a particularly preferred embodiment the d(0.5) value of the CSS particles is less than the mean diameter of a human enamel tubule. Enamel tubules typically have a mean diameter of from 50 to 100 nm. Thus the d(0.5) value of the CSS particles is preferably from 5 to 20 nm, optionally 5 to 12 nm. Preferably, when the CSS particles are intended to enter the enamel tubules, these particles are prepared from fined silica. Fumed silica consists of particles having a d(0.5) in the range of from 5 to 20 nm which agglomerate into larger particles having a d(0.5) in the micrometer range.

CSS particles may be spherical, or substantially spherical however it will be understood that the particles may have other shapes, for example rod, needle, or ellipsoidal shapes. The particles may have irregular shapes. The particles may also form larger size aggregates.

The metal silicate may comprise a plurality of monolayers of $M_2SiO_3 \cdot xH_2O$. The number of monolayers may be from 2 to 100, from 2 to 40, 2 to 12 or 12 to 40 monolayers.

The particle may comprise 2, 4, 16, 32 or 36 surface metal silicate monolayers.

The silica is preferably selected from the group consisting of a precipitated silica, a fumed silica and a fused silica.

Core shell silica particles preferably have a high surface charge density and ion exchange capacity. Optionally, the core shell silica particles have a total cationic exchange capacity of from 0.5 to 5.0 meq/g. Core shell silica particles with a high cationic exchange capacity are particularly preferred, since this enables the CSS to exchange metal ions such as Na+ on their surface for calcium ions in saliva, inhibiting the formation of tartar.

In one embodiment, the core shell silica particles have a turbidity of from 0.0 to 0.2 at a wavelength of from 300 to 800 nm using a 0.20 mm quartz UV optical cell. These particles may be described as translucent or transparent.

In another embodiment, the core shell silica particles have a turbidity of from 0.8 to 1.6 at a wavelength of from 300 to 800 nm using a 0.20 mm quartz UV optical cell. These particles may be described as semi-opaque.

In a further embodiment, the core shell silica particles have a turbidity of from 1.8 to 2.4 at a wavelength of from 300 to 800 nm using a 0.20 mm quartz UV optical cell. These particles may be described as opaque.

In preferred embodiments, the amount of core shell silica particles is 0.001 to 10 weight %, or 0.01 to 5 weight %, or 0.05 to 5 weight %, or 0.1 to 5 weight %, or 0.5 to 5 weight %, or 0.5 to 3 weight %, or 1 to 2 weight %, or about 1 weight % of the composition.

Orally Acceptable Carrier Vehicle

The oral care compositions of the invention include a vehicle or base into which the dye and core shell silica particles are incorporated. The carrier vehicle may be present in an amount of from 40 to 99 weight % or from 55 to 85 weight %, based on the total weight of the composition. It has been surprisingly discovered that when the dye is incorporated into a non-aqueous carrier containing little or substantially no water, the tooth whiteness effect is enhanced. In some embodiments the orally acceptable carrier vehicles comprises alcohols, polyhydric alcohols such as glycerol, sorbitol, xylitol, propylene glycol, polyols, ketones, aldehydes, carboxylic acids or salts thereof, amines, or mixtures thereof. In one embodiment the carrier comprises glycerol. Such materials typically also function as humectants.

In some aspects of the present invention, low amounts of water are present, e.g., from 3 weight % to 30 weight %, 5 to 17 weight %, 10 to 17 weight %, 5 to 15 weight %, 5 weight % to less than 10 weight %, 5 to 7 weight %, or about 7 weight %, about 10 weight %, or about 15 weight %.

It is surprising that the low water content of the compositions of the invention allows for enhanced delivery of the dye to the teeth, since the dyes are water soluble. It is not desired to be bound by any particular theory or mechanism, but it is believed that use of the compositions of the invention, with little or no water, drives the dye into the aqueous voids of the tooth enamel.

The orally acceptable carrier vehicle optionally can include various other ingredients which are typically incorporated into dentifrices. Examples of such other ingredients include carrier polymers, humectants, abrasives, thickener silicas or any combination of two or more thereof. The term "orally-acceptable" refers to a material or ingredient which can be applied to the oral cavity in a safe manner during normal use.

Carrier Polymers

Carrier polymers can comprise one or more anionic or nonionic polymers, and also may include additional polymers to adjust the viscosity of the formulation or enhance the solubility of other ingredients.

Suitable carrier polymers include polyethylene glycols, polysaccharides (e.g., cellulose derivatives, for example carboxymethyl cellulose, or polysaccharide gums, for example xanthan gum or carrageenan gum). Acidic polymers, for example polyacrylate gels, may be provided in the form of their free acids or partially or fully neutralized water soluble alkali metal (e.g., potassium and sodium) or ammonium salts. Anionic polymers may be present in an amount of from about 0.001 to about 5%, more particularly about 0.01 to 5%, more particularly about 0.05 to 4%, more particularly about 0.05 to 3% of the composition. Examples of such agents are disclosed in U.S. Pat. Nos. 5,188,821 and 5,192,531; and include synthetic anionic polymeric polycarboxylates, such as 1:4 to 4:1 copolymers of maleic anhydride or acid with another polymerizable ethylenically unsaturated monomer, preferably methyl vinyl etherimaleic anhydride having a molecular weight (M.W.) of about 30,000 to about 1,000,000, most preferably about 300,000 to about 800,000. These copolymers are available for example as Gantrez). e.g., AN 139 (M.W. 500,000), AN 119 (M.W. 250,000) and preferably S-97 Pharmaceutical Grade (M.W.

700,000) available from ISP Technologies, Inc., Bound Brook, N.J. 08805. Other operative polymers include those such as the 1:1 copolymers of maleic anhydride with ethyl acrylate, hydroxyethyl methacrylate, N-vinyl-2-pyrollidone, or ethylene, the latter being available for example as Monsanto EMA No. 1103, M.W. 10,000 and EMA Grade 61, and 1:1 copolymers of acrylic acid with methyl or hydroxyethyl methacrylate, methyl or ethyl acrylate, isobutyl vinyl ether or N-vinyl-2-pyrrolidone. Suitable generally, are polymerized olefinically or ethylenically unsaturated carboxylic acids containing an activated carbon-to-carbon olefinic double bond and at least one carboxyl group, that is, an acid containing an olefinic double bond which readily functions in polymerization because of its presence in the monomer molecule either in the alpha-beta position with respect to a carboxyl group or as part of a terminal methylene grouping. Illustrative of such acids are acrylic, methacrylic, ethacrylic, alpha-chloroacrylic, crotonic, beta-acryloxy propionic, sorbic, alpha-chlorsorbic, cinnamic, beta-styrylacrylic, muconic, itaconic, citraconic, mesaconic, glutaconic, aconitic, alpha-phenylacrylic, 2-benzyl acrylic, 2-cyclohexylacrylic, angelic, umbellic, fumaric, maleic acids and anhydrides. Other different olefinic monomers copolymerizable with such carboxylic monomers include vinylacetate, vinyl chloride, dimethyl maleate and the like. Copolymers contain sufficient carboxylic salt groups for water-solubility. A further class of polymeric agents includes a composition containing homopolymers of substituted acrylamides and/or homopolymers of unsaturated sulfonic acids and salts thereof, in particular where polymers are based on unsaturated sulfonic acids selected from acrylamidoalykane sulfonic acids such as 2-acrylamide 2 methylpropane sulfonic acid having a molecular weight of about 1,000 to about 2,000,000, described in U.S. Pat. No. 4,842,847, Jun. 27, 1989 to Zahid, incorporated herein by reference. Another useful class of polymeric agents includes polyamino acids containing proportions of anionic surface-active amino acids such as aspartic acid, glutamic acid and phosphoserine, (in addition to the basic amino acid polymers), e.g. as disclosed in U.S. Pat. No. 4,866,161 Sikes et al., incorporated herein by reference.

In preparing oral care compositions, it is sometimes necessary to add some thickening material to provide a desirable consistency or to stabilize or enhance the performance of the formulation. In certain embodiments, the thickening agents are carboxyvinyl polymers, carrageenan, hydroxyethyl cellulose and water soluble salts of cellulose ethers such as sodium carboxymethyl cellulose and sodium carboxymethyl hydroxyethyl cellulose. Hydroxyalkyl methyl cellulose may also be present in the oral composition. Natural gums such as karaya, gum arabic, and gum tragacanth can also be incorporated. Colloidal magnesium aluminum silicate or finely divided silica can be used as component of the thickening composition to further improve the composition's texture. In certain embodiments, thickening agents in an amount of about 0.05% to 5 weight %, more particularly about 0.5 to 5 weight % of the total composition are used. Orally acceptable carrier polymers for use in the invention are typically water soluble. Suitable orally acceptable carrier polymers for use in the invention will generally dissolve or disperse in water at a temperature of 25° C.

The amount of orally acceptable carrier vehicle polymer in compositions of the invention, whether enhancers, deposition aids, thickeners or the like, or of a combination thereof, suitably ranges from about 0.001 to 10 weight %, more particularly about 0.005 to 5 weight %, more particularly about 1 to 5 weight %, and more particularly about 1 to 3 weight %.

The composition may further comprise an additional agent selected from fluoride, arginine in free or orally acceptable salt form, an antibacterial agent, an anti-inflammatory agent, and a combination of two or more thereof.

The composition may be in the form of a dentifrice.

In one embodiment the composition is a toothpaste comprising one or more of an abrasive, a surfactant, a foaming agent, a vitamin, a polymer, an enzyme, a humectant, a thickener, an antimicrobial agent, a preservative, a flavoring, and/or a combination of two or more thereof.

The composition may be free from peroxide whitening agents.

Humectants

Within certain embodiments of the oral compositions, it is also desirable to incorporate a humectant to prevent the composition from hardening upon exposure to air. Certain humectants can also impart desirable sweetness or flavor to dentifrice compositions. The humectant, on a pure humectant basis, generally includes about 15% to about 70 weight % in one embodiment or about 30% to about 65 weight % in another embodiment by weight of the dentifrice composition. Suitable humectants include edible polyhydric alcohols such as glycerine, sorbitol, xylitol, propylene glycol as well as other polyols and mixtures of these humectants. Mixtures of glycerine and sorbitol may be used in certain embodiments as the humectant component of the toothpaste compositions herein.

Abrasives

The compositions of the invention may comprise a calcium phosphate abrasive, e.g., tricalcium phosphate ($Ca_3(PO_4)_2$), hydroxyapatite ($Ca_{10}(PO_4)_6(OH)_2$), or dicalcium phosphate dihydrate ($CaHPO_4.2H_2O$, also sometimes referred to herein as DiCal) or calcium pyrophosphate. The compositions may include one or more additional abrasives, for example silica abrasives such as precipitated silicas having a mean particle size of up to about 20 microns, such as Zeodent 115®, marketed by J. M. Huber. Other useful abrasives also include sodium metaphosphate, potassium metaphosphate, aluminum silicate, calcined alumina, bentonite or other siliceous materials, or combinations thereof. The silica abrasive polishing materials useful herein, as well as the other abrasives, generally have an average particle size ranging between about 0.1 and about 30 microns, about between 5 and about 15 microns. The silica abrasives can be from precipitated silica or silica gels, such as the silica xerogels described in U.S. Pat. No. 3,538,230, to Pader et al. and U.S. Pat. No. 3,862,307, to Digiulio, both incorporated herein by reference. Particular silica xerogels are marketed under the trade name Syloid® by the W. R. Grace & Co., Davison Chemical Division. The precipitated silica materials include those marketed by the J. M. Huber Corp. under the trade name Zeodent®, including the silica carrying the designation Zeodent 115 and 119. These silica abrasives are described in U.S. Pat. No. 4,340,583, to Wason, incorporated herein by reference. In certain embodiments, abrasive materials useful in the practice of the oral care compositions in accordance with the invention include silica gels and precipitated amorphous silica having an oil absorption value of less than about 100 cc/100 g silica and in the range of about 45 cc/100 g to about 70 cc/100 g silica. Oil absorption values are measured using the ASTA Rub-Out Method D281. In certain embodiments, the silicas are colloidal particles having an average particle size ($d(0.5)$) of about 3 microns to about 12 microns, and about 5 to about 10 microns. Low oil absorption silica abrasives particularly useful in the practice of the invention are marketed under the trade designation Sylodent XWA® by Davison Chemical Division of W.R. Grace & Co., Baltimore, Md. 21203. Sylodent 650 XWA®, a silica hydrogel composed of particles of colloidal silica having a water content of 29% by weight averaging about 7 to about 10 microns in diameter, and an oil absorption of less than about 70 cc/100 g of silica is an example of a low oil absorption silica abrasive useful in the practice of the present invention. The abrasive may be present in the oral care composition of the present invention at a concentration of about 10 to about 60% by weight, in other embodiment about 20 to about 45% by weight, and in another embodiment about 30 to about 50% by weight.

Product Form

Examples of suitable product forms for compositions of the invention include dentifrices. The term "dentifrice" generally denotes formulations which are used to clean the surfaces of the oral cavity. The dentifrice is an oral composition that is not intentionally swallowed for purposes of systemic administration of therapeutic agents, but is applied to the oral cavity, used to treat the oral cavity and then expectorated. Typically the dentifrice is used in conjunction with a cleaning implement such as a toothbrush, usually by applying it to the bristles of the toothbrush and then brushing the accessible surfaces of the oral cavity. Preferably the dentifrice is in the form of a paste or a gel (or a combination thereof).

Active Agents

The effective concentration of the active ingredients for optional use herein will depend on the particular agent and the delivery system used. It is understood that a toothpaste for example will typically be diluted with water upon use, while a mouth rinse typically will not be. Thus, an effective concentration of active in a toothpaste will ordinarily be 5-15× higher than required for a mouth rinse. The concentration will also depend on the exact salt or polymer selected. For example, where the active agent is provided in salt form, the counterion will affect the weight of the salt, so that if the counterion is heavier, more salt by weight will be required to provide the same concentration of active ion in the final product. Active agents can include one or more of a fluoride ion source, an anti-calculus agent, an amino acid, an antibacterial agent, and the like.

Arginine, where present, may be present at levels from about 1 to about 10 weight % for a consumer toothpaste or about 7 to about 20 weight % for a professional or prescription treatment product.

Fluoride where present may be present at levels of between about 25 ppm to about 25,000 ppm of fluoride ions. For consumer toothpastes, the fluoride level may be between about 500 to about 1600 ppm, or between about 500 to about 1000 ppm, or between about 1000 to about 1600 ppm, e.g., about 1100 ppm or 1450 ppm. The appropriate level of fluoride will depend on the particular application. A dentifrice or coating for professional application could have as much as about 5,000 or even about 25,000 ppm fluoride, e.g. a range of about 3,000 ppm to about 8,000 ppm fluoride.

Antibacterial agents may be included in the oral composition of the present invention and particularly noncationic halogenated diphenyl ethers agents which are desirable from considerations of effectiveness and safety, such as 2',4,4' trichloro-2 hydroxy-diphenyl ether (Triclosan) and 2,2'-dihydroxy-5,5' dibromophenyl ether. Other antibacterial agents, e.g. zinc salts, may be included in the compositions of the present invention. The antibacterial agent, when present in the oral composition, is present in concentrations of about 0.05 to about 2% by weight and preferably 0.1 to about 1% by weight. For example, a triclosan toothpaste may contain about 0.3 weight % triclosan.

Agents used to diminish teeth sensitivity such as potassium chloride, potassium nitrate, potassium citrate, dipotassium oxalate, or zinc phosphate may also be included in oral compositions of the present invention at concentrations of about 0.1 to about 10% by weight.

Fluoride Ion Source

The oral care compositions may further include one or more fluoride ion sources, e.g., soluble fluoride salts. A wide variety of fluoride ion-yielding materials can be employed as sources of soluble fluoride in the present compositions. Examples of suitable fluoride ion-yielding materials are found in U.S. Pat. No. 3,535,421, to Briner et al.; U.S. Pat. No. 4,885,155, to Parran, Jr. et al. and U.S. Pat. No. 3,678,154, to Widder et al., incorporated herein by reference. Representative fluoride ion sources include, but are not limited to, stannous fluoride, sodium fluoride, potassium fluoride, sodium monofluorophosphate, sodium fluorosilicate, ammonium fluorosilicate, amine fluoride, ammonium fluoride, and combinations thereof. In certain embodiments the fluoride ion source includes stannous fluoride, sodium fluoride, sodium monofluorophosphate as well as mixtures thereof. In certain embodiments, the oral care composition of the invention may also contain a source of fluoride ions or fluorine-providing ingredient in amounts sufficient to supply about 25 ppm to about 25,000 ppm of fluoride ions, generally at least about 500 ppm, e.g., about 500 to about 1000 ppm, e.g., about 1000 to about 1600 ppm, e.g., about 1100 ppm or 1450 ppm. The appropriate level of fluoride will depend on the particular application. A toothpaste for general consumer use would typically have about 1000 to about 1500 ppm, with pediatric toothpaste having somewhat less. A dentifrice or coating for professional application could have as much as about 5,000 or even about 25,000 ppm fluoride, e.g. a range of about 3,000 ppm to about 8,000 ppm fluoride.

Fluoride ion sources may be added to the compositions of the invention at a level of about 0.01 weight. % to about 10 weight. % in one embodiment or about 0.03 weight. % to about 5 weight. %, and in another embodiment about 0.1 weight. % to about 1 weight. % by weight of the composition in another embodiment. Weights of fluoride salts to provide the appropriate level of fluoride ion will obviously vary based on the weight of the counter ion in the salt.

Foaming Agents

The oral care compositions of the invention also may include an agent to increase the amount of foam that is produced when the oral cavity is brushed. Illustrative examples of agents that increase the amount of foam include, but are not limited to polyoxyethylene and certain polymers including, but not limited to, alginate polymers. The polyoxyethylene may increase the amount of foam and the thickness of the foam generated by the oral care carrier component of the present invention. Polyoxyethylene is also commonly known as polyethylene glycol ("PEG") or polyethylene oxide. The polyoxyethylenes suitable for this invention will have a molecular weight of about 200,000 to about 7,000,000. In one embodiment the molecular weight will be about 600,000 to about 2,000,000 and in another embodiment about 800,000 to about 1,000,000. Polyox® is the trade name for the high molecular weight polyoxyethylene produced by Union Carbide. The polyoxyethylene may be present in an amount of about 1% to about 90%, in one embodiment about 5% to about 50% and in another embodiment about 10% to about 20% by weight of the oral care carrier component of the oral care compositions of the present invention. The dosage of foaming agent in the oral care composition (i.e., a single dose) may be about 0.01 to about 0.9% by weight, about 0.05 to about 0.5% by weight, and in another embodiment about 0.1 to about 0.2% by weight.

Anticalculus Agents

The oral composition can include at least one anticalculus composition, such as one or more of the anticalculus compositions recited in U.S. Pat. No. 5,292,526 titled "Antibacterial Anti-plaque Anticalculus Oral Composition," which is incorporated herein by reference. In various embodiments, the anti-calculus composition includes one or more polyphosphates. The anti-calculus composition can include at least one wholly or partially neutralized alkali metal or ammonium tripolyphosphate or hexametaphosphate salt present in the oral composition at an effective anti-calculus amount. The anti-calculus composition can also include at least one water soluble, linear, molecularly dehydrated polyphosphate salt effective in an anticalculus amount. The anti-calculus composition can also include a mixture of potassium and sodium salts at least one of which is present in an effective anti-calculus amount as a polyphosphate anti-calculus agent. The anti-calculus composition can also contain an effective anticalculus amount of linear molecularly dehydrated polyphosphate salt anti-calculus agent present in a mixture of sodium and potassium salts. Other useful anticalculus agents include polycarboxylate polymers and polyvinyl methyl ether/maleic anhydride (PVME/MA) copolymers, such as GANTREZ®

Surfactants

The compositions useful in the invention may contain anionic and/or nonionic surfactants, for example:
i. water-soluble salts of higher fatty acid monoglyceride monosulfates, such as the sodium salt of the monosulfated monoglyceride of hydrogenated coconut oil fatty acids such as sodium N-methyl N-cocoyl taurate, sodium cocomonoglyceride sulfate,
ii. higher alkyl sulfates, such as sodium lauryl sulfate,
iii. higher alkyl-ether sulfates, e.g., of formula $CH_3(CH_2)_mCH_2(OCH_2CH_2)_nOSO_3X$, wherein m is 6-16, e.g., 10, n is 1-6, e.g., 2, 3 or 4, and X is Na or K, for example sodium laureth-2 sulfate ($CH_3(CH_2)_{10}CH_2(OCH_2CH_2)_2OSO_3Na$).
iv. higher alkyl aryl sulfonates such as sodium dodecyl benzene sulfonate (sodium lauryl benzene sulfonate)
v. higher alkyl sulfoacetates, such as sodium lauryl sulfoacetate (dodecyl sodium sulfoacetate), higher fatty acid esters of 1,2 dihydroxy propane sulfonate, sulfocolaurate (N-2-ethyl laurate potassium sulfoacetamide) and sodium lauryl sarcosinate.

By "higher alkyl" is meant, e.g., $C_{6-30}$ alkyl. In particular embodiments, the anionic surfactant is selected from sodium lauryl sulfate and sodium ether lauryl sulfate. The anionic surfactant may be present in an amount which is effective, e.g., >0.01% by weight of the formulation, but not at a concentration which would be irritating to the oral tissue, e.g., <10%, and optimal concentrations depend on the particular formulation and the particular surfactant. For example, concentrations used for a mouthwash are typically on the order of one tenth that used for a toothpaste. In one embodiment, the anionic surfactant is present in a toothpaste at from about 0.3% to about 4.5% by weight, e.g., about 1.5%.

Nonionic surfactants include nonanionic polyoxyethylene surfactants such as Polyoxamer 407, Steareth 30, Polysorbate 20, and PEG-40 castor oil and amphoteric surfactants such as cocamiopropyl betaine (tegobaine) and cocamidopropyl betaine lauryl glucoside condensation products of ethylene oxide with various hydrogen containing compounds that are reactive therewith and have long hydorphobic chains (e.g., aliphatic chains of about 12 to 20 carbon atoms), which condensation products ("ethoxamers") contain hydrophilic polyoxyethylene moieties, such as condensation products of poly (ethylene oxide) with fatty acids, fatty alcohols, fatty amides and other fatty moieties, and with propylene oxide and polypropylene oxides (e.g., Pluronic® materials).

The compositions of the invention may optionally contain mixtures of surfactants, e.g., comprising anionic surfactants and other surfactants that may be anionic, cationic, zwitterionic or nonionic. Generally, surfactants are those which are reasonably stable throughout a wide pH range. Surfactants are described more fully, for example, in U.S. Pat. No. 3,959,458, to Agricola et al.; U.S. Pat. No. 3,937,807, to Haefele; and U.S. Pat. No. 4,051,234, to Gieske et al., which are incorporated herein by reference. In certain embodiments, the anionic surfactants useful herein include the water-soluble salts of alkyl sulfates having about 10 to about 18 carbon atoms in the alkyl radical and the water-soluble salts of sulfonated monoglycerides of fatty acids having about 10 to about 18 carbon atoms. Sodium lauryl sulfate, sodium lauroyl sarcosinate and sodium coconut monoglyceride sulfonates are examples of anionic surfactants of this type. In a particular embodiment, the composition of the invention, e.g., Composition 1, et seq., comprises sodium lauryl sulfate.

The surfactant or mixtures of compatible surfactants can be present in the compositions of the present invention in about 0.1% to about 5.0%, in another embodiment about 0.3% to about 3.0% and in another embodiment about 0.5% to about 2.0% by weight of the total composition.

Flavoring Agents

The oral care compositions of the invention may also include a flavoring agent. Flavoring agents which are used in the practice of the present invention include, but are not limited to, essential oils as well as various flavoring aldehydes, esters, alcohols, and similar materials. Examples of the essential oils include oils of spearmint, peppermint, wintergreen, *sassafras*, clove, sage, *eucalyptus*, marjoram, cinnamon, lemon, lime, grapefruit, and orange. Also useful are such chemicals as menthol, carvone, and anethole. Certain embodiments employ the oils of peppermint and spearmint. The flavoring agent may be incorporated in the oral composition at a concentration of about 0.1 to about 5% by weight and about 0.5 to about 1.5 weight %. The dosage of flavoring agent in the individual oral care composition dosage (i.e., a single dose) may be about 0.001 to 0.05 weight % and in another embodiment about 0.005 to about 0.015 weight %.

Other Optional Ingredients

In addition to the above-described components, the embodiments of this invention can contain a variety of optional dentifrice ingredients some of which are described below. Optional ingredients include, for example, but are not limited to, adhesives, sudsing agents, sweetening agents, and additional coloring agents. These and other optional components are further described in U.S. Pat. No. 5,004,597, to Majeti; U.S. Pat. No. 3,959,458 to Agricola et al. and U.S. Pat. No. 3,937,807, to Haefele, all being incorporated herein by reference.

Process for the Preparation of the Composition

In a further aspect, the present invention provides a process for the preparation of a composition as defined in any preceding claim, the process comprising:

i) admixing an amount of silica particles in water with an amount of a base, the base comprising a metal ion, to produce the core shell silica particles, wherein each core shell silica particle comprises a silica core, and a surface of the silica core is etched with metal silicate;
ii) admixing the core shell silica particles formed in step i) with an orally acceptable carrier vehicle comprising a non-aqueous solvent, a dye having a blue to blue-violet color with a hue angle in the CIELAB system ranging from 200 to 320 degree, and an amount of water to produce a composition comprising from 3 weight % to 30 weight % water.

Step i) of the invention may comprise admixing an amount of $SiO_2$ particles in water with an amount of NaOH in solid or aqueous form, with or without a humectant, to produce the core shell silica particle. Sodium hydroxide reacts with the surface of the $SiO_2$ particle to etch a shell of layers(s) of $Na_2SiO_3$ as follows:

$$SiO_2 + 2NaOH \rightarrow Na_2SiO_3 + H_2O$$

As can be seen from the reaction scheme, no NaOH will result in no change to the silica, whereas at the other extreme, complete reaction with 2 moles of NaOH per 1 mole of silica will result in the complete conversion into $Na_2SiO_3$. In order, to obtain the core shell particles of the invention, the reaction process must be controlled so as to not achieve complete conversion into $Na_2SiO_3$.

The process for making the core shell silica particles comprises of etching the original silica in order to form $Na_2SiO_3$ layers, i.e. the $Na_2SiO_3$ layers are not additional layers coated on top of the surface of the silica.

As the covalent bonds of the $SiO_2$ network are turned into ionic bonds between $Na^+$ and $SiO_3^{2-}$, the surface becomes polarized and adsorbs water and the humectant to produce the core shell silica particle.

The process may comprise a further step after step i) and prior to step ii) of reacting the core shell silica particles formed in step i) with a metal salt comprising a second metal ion to form core shell silica particles comprising silicate of the second metal ion on a surface of the silica core.

The base may be in solid or aqueous form. The base is preferably selected from the group consisting of sodium hydroxide, potassium hydroxide, calcium hydroxide, barium hydroxide, ammonium hydroxide, sodium carbonate, potassium carbonate, trisodium phosphate, disodium phosphate, potassium phosphate, dipotassium phosphate, tetrasodium pyrophosphate, and tetrapotassium pyrophosphate. A particularly preferred base is sodium hydroxide, most preferably 50% aqueous sodium hydroxide solution.

Step i) may be carried out at a temperature in the range of from 17° C. to 90° C. In one embodiment the process is carried out at room temperature, i.e. 20 to 26° C. In another embodiment step i) is carried out at a temperature of from 70 to 90° C. When preparing the core shell silica particles on an industrial scale, the mixer used to mix the reactants, such as a Lee mixer (Lee Industries), is preferably not heated up.

In one embodiment, in step i) the base is sodium hydroxide and the process is carried out at a temperature of from 70 to 90° C. In another embodiment, in step i) the base is potassium hydroxide and the process is carried out at room temperature. This is embodiment is advantageous because the use of the more reactive potassium hydroxide means that heating is not required.

The formation of the core shell silica particles in step i) is typically complete after a time period of 2 hrs.

The weight ratio of the amount of base to the amount of silica particles in step i) may be from 1:1 to 1:20. The weight ratio for the amount of base to the amount of silica particles may be from 1:1 to 1:3.

The turbidity of the core shell silica particles is decreased by increasing the weight ratio for the amount of base to the amount of silica particles.

An average depth of from 1 to 15 nm of silica may be removed from the surface of the silica particle to form the silica core, and metal silicate is formed on top of the silica core in step i). The average depth of silica removed typically increases as the weight ratio for the amount of base to the amount of silica particles increases. The d(0.5) of the silica core may be from 1 to 15 nm less than the d(0.5) of the silica particles of the starting material. The d(0.5) of the silica core may be about 2 nm less than the d(0.5) of the silica particles of the starting material. The d(0.5) particle diameter of the silica core may be about 6 nm less than the d(0.5) of the silica particles of the starting material. There is a greater percentage reduction in particle diameter for rigid silica particles such as fumed silica than for porous silica particles such as high cleaning silica. For example, for fumed silica the percentage reduction in particle diameter (d(0.5)) may be approximately 15%, whilst for porous high cleaning silica the percentage reduction in particle diameter (d(0.5)) may be approximately 0.06%.

The formation of the core shell silica particles of the invention described above can be effected by manipulating the amount of based used, the amount of humectant used, the amount of metal salt used, and varying the temperature of the reaction.

The formation of the core shell particles can be monitored by determining the pH of the reaction mixture. In one embodiment, step i) is complete when the pH of the reaction mixture decreases by at least 0.5 pH units from the initial mixture of reactants. In another embodiment, step i) is complete when the pH of the reaction mixture decreases by at least 0.8 pH units from the initial mixture of reactants. Typically, step i) is complete when the pH of the reaction mixture is about 11. The process may comprise a further step after the step of forming the core shell particles of adjusting the pH of the reaction mixture to from 7 to 8. The pH of the reaction mixture is typically adjusted using acid. The acid may be selected from the group consisting of phosphoric acid, citric acid and lactic acid.

The formation of the core shell particles in step i) can also be monitored by determining the conductivity of the reaction mixture. The end point of the process results when the conductivity of the reaction mixture decreases by at least 250 micro Siemens/cm (μS/cm) because the electric charges transfer from highly mobile ions (NaOH) to much less mobile silica surface (mobility≈0). In yet another embodiment, the end point of the process results when the conductivity of the reaction mixture decreases by 250-400 μS/cm. Typically, the core shell silica particles are formed when the conductivity of the reaction mixture decreases by at least 2 milliSiemens/cm (mS/cm). Usually, the core shell silica particles are formed when the conductivity of the reaction mixture decreases by at least 5 mS/cm.

In an embodiment, the core shell silica particles of the invention are formed when at least 1-6% of each of the silica particle starting material has been etched with one or more layers of silicate. In another embodiment, the core shell silica particles of the invention are formed when at least 2.5-5% of each of the silica particle starting material has been etched with one or more layers of $Na_2SiO_3$. In another embodiment, the core shell silica particles of the invention are formed when at least 3.5-4% of each of the silica particle starting material has been etched with one or more layers of silicate.

It is understood that while general attributes of each of the above categories of materials may differ, there may be some common attributes and any given material may serve multiple purposes within two or more of such categories of materials. All of the ingredients in the compositions may have functions in addition to their primary function, and may contribute to the overall properties of the composition, including its stability, efficacy, consistency, mouthfeel, taste, odor and so forth. Preferably, the carrier is selected for compatibility with other ingredients of the composition.

As used throughout, ranges are used as shorthand for describing each and every value that is within the range. Any value within the range can be selected as the terminus of the range. In addition, all references cited herein are hereby incorporated by referenced in their entireties. In the event of a conflict in a definition in the present disclosure and that of a cited reference, the present disclosure controls.

Unless otherwise specified, all percentages and amounts expressed herein and elsewhere in the specification should be understood to refer to percentages by weight based on the total weight of the composition. The amounts given are based on the active weight of the material. For convenience, components of the composition of invention are expressed in the singular; however it is to be understood that mixtures of components are encompassed by use of the singular expression, for example, "an orally acceptable carrier polymer" may include mixtures of two or more polymers described herein.

The invention also includes a method for whitening teeth comprising administering the composition of the invention to the oral cavity of a subject in need thereof. In one embodiment of the invention, the method provides a teeth whitening effect of at least a 20% increase in tooth surface whiteness which lasts for up to four hours.

Embodiments of the present invention are further described in the following examples. The examples are merely illustrative and do not in any way limit the scope of the invention as described and claimed.

EXAMPLES

Example 1

It has been found that when the carrier system for a blue dye is primarily non-aqueous the ability of the blue dye to increase the whiteness of teeth is enhanced. We have shown the increase in tooth whiteness is greater when blue dye is formulated into a non-aqueous solution of glycerin as compared to when the blue dye is delivered from an aqueous solution.

TABLE 1

|  | Δb* | ΔWIO |
|---|---|---|
| Dye control in AQ | −0.9 | 3.9 |
| Dye control in non-AO | −2.7 | 11.7 |

In addition, bioadhesive materials such as VM/MA Copolymer (Gantrez) and cross-linked PVP have been demonstrated to increase blue dye retention on teeth. The inventors have surprisingly found that when the surface chemistry of silica is modified with a strong base the resulting particle can also increase the retention of blue dye on the surface. This novel material consisting of a silica core etched with silicate is referred to as core shell silica (CSS).

TABLE 2

| Non-AQ Solution | Δb* initial | ΔWIO initial | Δb* after 30 min soak | ΔWIO after 30 min soak |
|---|---|---|---|---|
| Dye Control | −2.7 | 5.5 | 0.4 | −1.6 |
| Dye + Gantrez | −3.2 | 13.7 | −0.5 | 4.1 |
| Dye + Coreshell Silica | −2.5 | 11.0 | −0.8 | 5.1 |

The above experiments found that CSS was more effective than a Gantrez containing solution of dye in glycerin in the delivery and retention of blue dye to teeth for an increase in tooth whitening. In addition to simple solutions, we have found CSS can be extremely effective at maintaining increased in tooth whitening when delivered from a dentifrice formula having a critical level of water.

Example 2

Experimental Method for Evaluating Retention of Blue Dye on Teeth and Resulting Tooth Whiteness The roots of human third molars were removed and the tooth was bisected from the crown through the root. Each half of the tooth was mounted in methacrylate resin and then secured in a brushing tray, enamel side facing out, using a thermal impression compound. Four teeth were mounted per tray. The teeth were brushed for 10 minutes with a 1:2 (w/w) silica toothpaste slurry to remove any extrinsic surface stains, rinsed with deionized water, dried with cool air, and baseline CieLab measurements were recorded with a spectrophotometer (Spectroshade Micro, MHT technologies). Teeth were submerged in saliva (9 mL/tray), aged at 37° C. with gentle agitation for 15 minutes. The test toothpaste (6 g) was then added to the tray already containing 9 mL saliva, the teeth were brushed for 2 minutes, rinsed with 100 mL deionized water, dried with cool air, and CieLab measurements were recorded. The teeth were aged in saliva for 10 minutes or 30 minutes. Teeth were rinsed and dried with cool air before CieLab measurements were recorded at each time-point during the soaking cycle. Δb* is reported and is the change in the yellow-blue axis in CieLab color space. This is the metric by which the deposition of blue dye can be quantified. The Ab* reported is the difference between the b* values of the tooth after surface stains are removed to that after brushing with the product containing blue dye. A change in a whiteness index (WIO) is also be reported to show that the deposition of blue dye results in an increase in the whiteness of a tooth.

TABLE 3

| Formula composition with ranges | | |
|---|---|---|
| Ingredient | Target Weight % | Weight % Range |
| Glycerin | 58.86 | |
| High Cleaning Silica | 20 | 10-25 |
| Water | 7 | 3-30 |
| Thickening Silica | 4 | 0-6 |
| Polyethylene Glycol | 3 | |
| Sodium Lauryl Sulfate | 1.5 | |
| Coreshell Silica | 2 | 1.5-5 |

TABLE 3-continued

Formula composition with ranges

| Ingredient | Target Weight % | Weight % Range |
|---|---|---|
| Titanium dioxide | 0.5 | |
| Sodium Saccharin | 0.5 | |
| Xanthum Gum | 0.3 | |
| Sodium Carboxymethylcellulose | 0.25 | 0.1 |
| Sodium Fluoride | 0.24 | |
| FD&C Blue#1 | 0.05 | 0.02-2 |

Core shell Silica and blue dye vs. matching formula without core shell silica. Both formulas contain 7% water and 0.05% FD&C blue #1 dye.

TABLE 4

| | Δb* | | | ΔWIO | | |
|---|---|---|---|---|---|---|
| | Initial | 10 min saliva | 30 min saliva | Initial | 10 min saliva | 30 min saliva |
| 0% CSS | −1.3 | 0.0 | 0.4 | 7.04 | 3.33 | 1.75 |
| 2% CSS | −1.4 | −0.6 | −0.3 | 5.95 | 4.71 | 3.34 |

The data in table 4 demonstrate that the addition of CSS to the formula results in similar deposition of blue dye but an increase in the retention time of the dye on teeth.

TABLE 5

CSS vs. Gantrez

| | Δb* | | | ΔWIO | | |
|---|---|---|---|---|---|---|
| | Initial | 10 min saliva | 30 min saliva | Initial | 10 min saliva | 30 min saliva |
| 2% CSS | −1.4 | −0.6 | 0.3 | 5.95 | 4.71 | 3.34 |
| 2% Gantrez | −0.8 | −0.1 | −0.2 | 4.95 | 2.92 | 2.61 |

At 2% loading in low water (7%) dentifrice, CSS provides superior blue dye delivery and retention to Gantrez.

TABLE 6

2% xPVP with 0.05%, 0.10% and 0.15% FD&C Blue #1

| | Δb* Initial | ΔWIO Initial |
|---|---|---|
| 0.05% FD&C Blue #1 | −1.4 | 6.0 |
| 0.10% FD&C Blue #1 | −2.5 | 7.8 |
| 0.15% FD&C Blue #1 | −2.5 | 9.9 |

It can be seen from the data in Table 6 that 2% core shell silica provides a dose response in whitening efficacy with various levels of blue dye.

In a dentifrice formula having low water (approximately 7%) and CSS, increasing the amount of blue dye will increase the amount of dye deposited on teeth and the perceived whiteness of the teeth. At only 0.05% FD&C blue number one there is a significant change in tooth whiteness from the deposition of blue dye.

In summary, we have shown that a low water formula containing CSS can improve the retention of blue dye on teeth. For optimal blue dye delivery a minimal amount of water to activate the CSS is required.

As those skilled in the art will appreciate, numerous changes and modifications may be made to the embodiments described herein without departing from the spirit of the invention. It is intended that all such variations fall within the scope of the appended claims.

What is claimed is:

1. A tooth whitening oral care composition comprising:
   (i) a dye having a blue to blue-violet color with a hue angle in the CIELAB system ranging from 200 to 320 degrees;
   (ii) core shell silica particles, wherein each core shell silica particle comprises a silica core, and a surface of the silica core is etched with metal silicate;
   (iii) an orally acceptable carrier vehicle comprising a non-aqueous solvent; and
   wherein the composition comprises water in an amount of from 3 weight % to 30 weight %.

2. The composition according to claim 1, wherein the metal silicate for each core shell silica particle is:
   i) a metal silicate of a monovalent metal ion; or
   ii) a metal silicate of a monovalent metal ion and one or more of a of a divalent metal ion, a trivalent metal ion, and a tetravalent metal ion.

3. The composition according to claim 2, wherein the monovalent metal ion is a group I metal ion.

4. The composition according to claim 1, wherein the metal silicate comprises the formula $M^1_2SiO3.x\ H_2O$, wherein $M^1$ is a monovalent metal ion, optionally a group I metal, and x is from 0 to 10; and the outer 10 nm depth of a core shell silica particle comprises from 0.1 to 10 weight % $M^1_2SiO3.xH_2O$.

5. The composition according to claim 1, wherein the outer 10 nm depth of a core shell silica particle has the general formula:

$$(SiO_2)_p[O_o{*}N^+{}_nH^+{}_hOH^-{}_j)].qH_2O$$

wherein O* is oxygen in the silicate form; N is a group I metal ion; p, o, n, h, j and q are the atomic percentages of each component; and the total charge of each core shell silica particle is zero.

6. The composition according to claim 1, wherein the metal silicate comprises a silicate of a group 2 metal ion, a transition metal ion, a group 13 metal ion, a group 14 metal ion or mixtures thereof.

7. The composition according to claim 1, wherein the metal silicate comprises the formula $M^2SiO3.x\ H_2O$, wherein $M^2$ is a divalent metal ion selected from the group consisting of Zn, Ca, Mg, Sn, and Sr, and x is from 0 to 10.

8. The composition according to claim 6, wherein the outer 10 nm depth of each particle has the general formula:

$$(SiO_2)_p[O^*{}_oN^+{}_nM^{2+}{}_mU^{3+}{}_uV^{4+}{}_vH^+{}_hOH^-{}_j].qH_2O$$

wherein O* is oxygen in the silicate form; N is a monovalent metal ion; M is a divalent metal ion; U is a trivalent metal ion; V is a tetravalent metal ion; p, o, n, m, u, v, h, j and q are the atomic percentages of each component; and the total charge of each core shell silica particle is zero.

9. The composition according to claim 1, wherein the d(0.5) value of the core shell silica particles ranges from 5 nm to 50 μm.

10. The composition of claim 1, wherein the amount of core shell silica particles is 0.001 to 10 weight % of the composition.

11. The composition of claim 1, wherein the dye comprises from 0.001 to 2 weight % of the composition.

12. The composition according to claim 1, wherein the dye comprises a metal ion.

* * * * *